United States Patent [19]

Latzke et al.

[11] Patent Number: 4,994,049
[45] Date of Patent: * Feb. 19, 1991

[54] DEVICE FOR APPLYING A SUBSTANCE TO THE SKIN

[76] Inventors: Arno W. Latzke; Ralf Latzke; Gert Latzke, all of Mühltobel 946, CH-9429 Zelg/Wolfhalden, Switzerland

[ * ] Notice: The portion of the term of this patent subsequent to Feb. 6, 2007 has been disclaimed.

[21] Appl. No.: 436,709

[22] Filed: Nov. 15, 1989

Related U.S. Application Data

[63] Continuation of Ser. No. 245,923, Sep. 16, 1988, Pat. No. 4,898,592, which is a continuation of Ser. No. 42,344, Apr. 24, 1987, abandoned.

[30] Foreign Application Priority Data

Aug. 23, 1986 [DE] Fed. Rep. of Germany ....... 3628688
Aug. 30, 1986 [DE] Fed. Rep. of Germany ....... 3629565
Feb. 18, 1987 [EP] European Pat. Off. .......... 87102306

[51] Int. Cl.$^5$ ............................................. A61F 13/02
[52] U.S. Cl. ..................................... 604/307; 128/156; 424/448; 424/449
[58] Field of Search .......................... 604/304–308, 604/890.1, 892.1; 128/155, 156; 424/448, 449, 447

[56] References Cited

U.S. PATENT DOCUMENTS

| | | | |
|---|---|---|---|
| 1,862,122 | 6/1932 | Schrader | 604/307 |
| 2,344,021 | 3/1944 | Bouziane | 604/305 |
| 3,026,874 | 3/1962 | Stevens | 604/305 |
| 3,598,122 | 8/1971 | Zaffaroni . | |
| 3,674,027 | 7/1972 | Fleischmajer | 604/304 |
| 3,777,754 | 12/1973 | Plachy . | |
| 3,837,340 | 9/1974 | Counter | 604/307 |
| 4,230,105 | 10/1980 | Harwood . | |
| 4,286,592 | 9/1981 | Chandrasekaran . | |
| 4,297,995 | 11/1981 | Golub . | |
| 4,460,372 | 7/1984 | Campbell et al. . | |
| 4,564,010 | 1/1986 | Coughlan et al. . | |
| 4,595,391 | 6/1986 | Abplanalp . | |
| 4,605,399 | 8/1986 | Weston et al. | 604/890.1 |
| 4,687,476 | 8/1987 | Pailin | 604/307 |
| 4,695,277 | 9/1987 | Lauk | 604/304 |
| 4,743,249 | 5/1988 | Loveland | 604/304 |
| 4,765,986 | 8/1988 | Liedtke | 424/448 |
| 4,822,617 | 4/1989 | Panoz | 604/304 |
| 4,898,592 | 2/1990 | Latzke et al. | 604/307 |

FOREIGN PATENT DOCUMENTS

| | | |
|---|---|---|
| 0136393 | 4/1985 | European Pat. Off. . |
| 2301821 | 8/1974 | Fed. Rep. of Germany . |
| 2722273 | 11/1978 | Fed. Rep. of Germany . |
| 2561505 | 9/1985 | France . |

Primary Examiner—Stephen C. Pellegrino
Assistant Examiner—Ralph A. Lewis
Attorney, Agent, or Firm—Wegner, Cantor, Mueller & Player

[57] ABSTRACT

A device and method for applying substances to skin using an absorptive carrier in a laminate support. The support includes a first foam layer having a thickness of about 1 to 6 mm, a second foam layer having a thickness of about 1 to 6 mm bonded to the first foam layer and having a portion removed to house the carrier, and a metal foil between the first foam layer and the carrier housed in the second foam layer. The surface of the second foam layer which faces the skin may be surface texturized or have a fabric laminated thereon. A substance, such as a transdermally absorbable medicinal oil, is applied to the carrier and the carrier is replaceably inserted in the support. The support is then applied to the skin.

14 Claims, 4 Drawing Sheets

DEVICE FOR APPLYING A SUBSTANCE TO THE SKIN

This application is a continuation of Ser. No. 245,923, filed Sept. 16, 1988, now U.S. Pat. No. 4,898.542 which is a continuation of Ser. No. 042,344, filed Apr. 24, 1987, now abandoned.

The present invention relates to a device for the application of transdermally absorbable active substances which allows an intensive and sustained action of the transdermally absorbable active substances over a long period of time and increases the efficiency thereof by simultaneous action of heat.

BACKGROUND OF THE INVENTION

A number of pains, cramps and convulsive disorders are caused by an insufficient or non-uniform blood flow in the outer skin. In many cases alleviation, improvement or even healing may be achieved by a uniform application of heat. The treatment with infrared radiation, warming bottles, heating pads, hot packs and cataplasms always involves considerable trouble and therefore is not always or readily practicable.

It is also known that transdermally absorbable active substances such as, more specifically, oils of officinal herbs, are therapeutically active, particularly when they can display their action over a sufficiently long period of time and have the opportunity of penetrating into the skin. There has already been a long search for possibilities of enhancing the efficiency of the transdermally absorbable active substances.

From the EP-A- 0 0163 045 there are known means for heat insulation and distribution, more specifically of heat of the body, on areas of the outer skin which means consist of a laminate comprising a foam layer, a flexible heat-conducting metal layer and a further foam layer These means have already proven to be valuable in the form of warming plasters, pads, mats etc.

SUMMARY OF THE INVENTION

It is the object of the present invention to combine said principle of heat therapy with the principle of the application of transdermally absorbable active substances, more specifically of oils from officinal herbs, in order to enhance and optimize the therapeutic activity.

Surprisingly, that object can be effectively and readily attained using means for the application of transdermally absorbable active substances, which means consist of at least one replaceable carrier (1) impregnated with the transdermally absorbable active substances and a support (2) for the carrier consisting of a laminate comprising (a) a closed-cell polyethylene foam layer (3) having a thickness of 1 to 5 mm, (b) a flexible heat-conductive metal foil (4), (c) a closed-cell polyethylene foam layer (5) having a thickness of 1 to 4 mm, which may optionally be colored, (d) a closed-cell polyethylene foam layer (6) having a thickness of 1 to 4 mm, which may optionally be surface-texturized, from which at least one portion (7), preferably in pinked shape, has been punched, the size of the area of the portion (7) being equal to or slightly larger than that of the carrier (1), or (a) a closed-cell polyethylene foam layer (3) having a thickness of 2 to 5 mm, (b) a flexible heat-conductive metal foil (4), (c) a closed-cell polyethylene foam layer (6) having a thickness of 2 to 5 mm, which may optionally be surface-texturized, from which at least one portion (7), preferably in pinked shape, has been punched, the size of the area of the portion (7) being equal to or slightly larger than that of the carrier (1), or (a) a closed-cell polyethylene foam layer (3) having a thickness of 2 to 6 mm, which may optionally be colored, (b) a closed-cell polyethylene foam layer (6) having a thickness of 2 to 5 mm, which may optionally be surface-texturized, from which at least one portion (7), preferably in pinked shape, has been punched, the absorptive carrier (1) on one side being firmly bonded to a flexible heat-conductive metal foil (4).

DETAILED DESCRIPTION

To allow easier attachment to the body, the means preferably have a fabric layer (8) on the foam layer (3), which preferably consists of Borsched nylon. This fabric layer allows the means of the invention to be attached to the body by use of skin-compatible self-adhesive plasters or elastic bandages having Velcro strip fasteners.

The device of the invention may be manufactured in the form of plasters, head-bands or pads, with head-bands and pads comprising several punched pieces (7) and carriers (1) impregnated with transdermally absorbable active substances and replaceably inserted therein.

As the carriers (1) there may preferably be used non-woven fabrics and, more specifically, any skin-compatible random laid nonwoven fabric having a sufficient rigidity which can be impregnated with the transdermally absorbable active ingredients. However, basically any other sufficiently rigid skin-compatible absorptive carriers which are resistant to transdermally absorbable active substances such as, open-cell foams, fabric etc. may be used. The shape of said impregnated carriers may be selected as desired and, for example, be square, rectangular or polygonal. Particularly simple and preferred is the circular shape. These carriers impregnated with transdermally absorbable active substances either may be freshly prepared by the user or may be supplied sealed in a bag—like refreshment cloths — from the manufacturer.

The size of the punched pieces (7) is equal in area or slightly larger than that of the carrier (1) and is preferably pinked. This shape provides a good support of the carrier in the recess and, in addition, favors the formation of air chambers at the margin of the carrier in which vapors of the transdermally absorbable substance may accumulate.

The closed-cell polyethylene foam layers (3), (5) and (6) may vary in thickness within the ranges as indicated between 1 and 5 mm or 1 and 6 mm, respectively, while the laminate altogether should be between 5 and 12 mm, and preferably between 6 and 10 mm, in thickness. Thinner laminates are difficult to manufacture and do not provide sufficient storage of heat. Thicker laminates will be too rigid and unhandy and too bulky.

As the flexible heat-conductive metal foil there is mainly used aluminum foil which is preferably 20 to 50 micrometers in thickness.

In a simpler embodiment preferred for manufacturing, the foam layer (5) is omitted so that the carrier (1) has direct contact with the metal foil (4). This may result in even a more rapid and higher warming of the carrier (1) and, thus, the effect is induced more rapidly and is stronger.

It is also possible to omit the metal film (4) in the support laminate (2) altogether, if the absorptive carrier on one side is firmly bonded to the flexible heat-conductive metal foil (4). In this embodiment, it is preferred that the two remaining foam layers (3) and (6) are different in color. Furthermore, in this embodiment, more specifically the layer (3) is selected so that it is thicker and/or made of a foam having coarser pores which has a higher heat insulation capacity The astonishing high efficiency of the inventive device is due to the following mechanism of action: As is the case with the means according to EP-A 0 163 045, the total laminate of the support (2) causes a good storage and distribution of the body heat to be effected. It has been shown that the feedback of heat to the body is particularly high in the punched portion (7). It is exactly this location where the carrier (1) impregnated with the transdermally absorbable active substances is situated, so that the transdermally absorbable active substances are warmed to a particularly high degree. This results in an increase of the vapor pressure of the transdermally absorbable active ingredients and an increased activity thereof in the area of the punched portions (7). In the air chambers close to the margin of the carrier the vapors of the transdermally absorbable active ingredients can accumulate so that they can display their activities over an extended period of time. The metal foil (4) acts at the same time as a baffle and prevents the vapors from prematurely escaping through the foam.

As it is preferred that the foam layer (6) contiguous to the skin is surface-texturized, some partial aeration and ventilation takes place so that an undesired sweat formation is suppressed. Due to this surface-texturizing, a portion of the vapors of the transdermally absorbable active substance can display their effects beyond the punching area Thus, the surface-texturizing preferably is in a square pattern spaced 1 to 3 mm apart. The grooves may be about 0.5 to 2 mm in depth. Instead of surface-texturizing, it is also possible to laminate the layer (6) with a fabric layer.

Measurements of the skin temperature under the action of the device of the invention have resulted in the finding that strongest heating occurs at the margins of the carrier (1), namely in the aeration chambers. This result can be explained only by the fact that at said location there is a minimum heat insulation so that the heat collected around the support (2) can be passed back to the body relatively undisturbed and at these locations the vapors of the transdermally absorbable active substances can act on the skin at a relatively high concentration.

In the manufacture of the support (2), there basically exists a possibility of integrally making the polyethylene foam layers (5) and (6), or (4) and (6), or even (3) and (6), respectively, and then therefrom to punch the portion (7) in such a manner that still up to 4 mm of the foam layer can remain between the support (1) and the metal foil (4). However, from the standpoint of manufacturing engineering such a procedure will be substantially more difficult than to laminate the respective two partial layers to each other as set forth hereinabove. This has another advantage in that the foam layers (5) and/or (3), respectively, may be colored, so that the punched portion (7) becomes clearly visible. This facilitates inserting the carrier (1) into the punched portion. Instead of punching said portion (7), it is of course also possible to hot-emboss said portion; which procedure, however, will hardly produce sharper pinks. In order to effect an improved attachment of the carrier (1) to the support (2), an impact adhesive or a double-sided adhesive film may be employed.

After the application, the carriers (1) will be discarded in most of the cases, whereas the support (2) may frequently be re-used. It may also be washed at 30° C. and thereby be kept in hygienic conditions.

The transdermally absorbable active substances may include, for example, liquids such as oils, but also tablets, pastes and powders if they have a sufficiently high vapor pressure. More particularly, oils of medicinal herbs may be employed. The preferred oils of medicinal herbs include ethereal oils such as camphor oil, green oil, lavender oil, peppermint oil, rosemary oil and turpentine oil as well as mixtures thereof. These oils are administered under condition of long-term warming for a therapeutic treatment of muscle and joint pain, lumbago, sciatica, intervertebral disk and rheumatic problems. They may further be employed for the prophylaxis and after-treatment of sports injuries, strains and contusions. In all these cases there is an increase in the tissue metabolism and an improved blood flow. Thus, the means of the invention constitute an excellent applicator, more specifically for medicinal oils and their vapors, whereby the efficiency is intensified and prolonged.

When the means according to the invention were tested, it was found that, particularly upon repeated use of the support, the carriers are no longer sufficiently supported and tend to come loose or displaced from their pre-determined positions. Although, basically, the carrier may be attached to the support by an impact adhesive or a piece of double-sided adhesive film, the following additional fastening means have proven to be better suitable. Velcro strip fasteners (13) are attached to the surface facing the support (2) of the carrier (1) as well as to the surface facing the carrier (1) A preferred embodiment consists of a magnetically adhesive metal plate (9) or a magnetically adhesive metal wire (10) attached to the surface facing the support (2) of the carrier (1), and in the support (2) there is attached facing the carrier a magnetic foil (11), which has been alternatingly positively and negatively permanently magnetized in the form of stripes, the distance of the magnetized bands from one another being between 3 and 10 mm.

The reversible attachment using a Velcro strip fastener is relatively simple and inexpensive to effect. However, the Velcro strip fastener has the drawback of that it is rather bulky and, thus, results in an undesired bulging of the device of the invention. Thus, one will accept this drawback only for devices in which a higher total thickness is acceptable.

The attachment using a magnetically adhesive metal plate (9) or a magnetically adhesive metal wire (10) has been shown to be particularly advantageous, since these metal fastening means may be readily attached to the surface facing the support (2) of the carrier (1), which is the surface remote from the body surface. This may be effected, for example, by interbonding with the nonwoven material or adhesion bonding thereto. In the embodiment in which the absorbable carrier (1) is on one side firmly bonded to the flexible heat-conductive metal foil (4), it is possible to insert the metal plate 9 or the metal wire (10) between the carrier and the metal foil.

As the magnetically adhesive metal plate or magnetically adhesive metal wire there may be used in particular iron, but also other ferromagnetic alloys or metals. When iron or steel are employed, it may be expedient, for reasons of protection from corrosion, to use iron plates or iron wires the surfaces of which have been zinc-plated or otherwise protected from corrosion.

As the magnetic foils, which have been alternatingly positively and negatively permanently magnetized in stripe form and wherein the distance of the magnetized stripes from one another is between 3 and 10 mm, there are suitable commercially available magnetic foils which are supplied in thicknesses of between 0.5 and 2 mm, and preferably between 1.0 and 1.5 mm, and have been alternatingly magnetized in the desired manner. The stripes may be linear or circular so that the magnetic stripes are arranged as concentric rings.

The distance of the magnetized stripes of between 3 and 10 mm ensures a good adhesion of the metal plates or of the metal wire to be effected due to magnetic attraction, even if they are not close to each other. This is due to the fact that stripe-shaped magnetic foils alternatingly positively and negatively permanently magnetized produce a sufficiently strong magnetic field even at a distance of some millimeters.

The size of the plate (9) may be larger or smaller than the size of the magnetic foil (11). It is preferred that the size of the magnetic plate is of the same order of magnitude as the punched portion (7). Using larger magnetic foils requires higher technical and material expenses. Magnetic foils (11) too small in dimensions fail to ensure a sufficient magnetic attraction of the metal plate (9) or of the metal wire (10).

Although it would basically be possible to interchange the positions of metal plate (9) or of metal wire (10), respectively, with the position of the magnetic foil (11), this would in fact mean that the carrier, only used once, would be disposed of together with the relatively expensive magnetic foil, whereas in the claimed embodiment the magnetic foil can be used several times together with the support (2).

It has also been shown that in some cases it may be advantageous in the device of the invention to cover the surface of the support (2) facing the skin with a skin-compatible material (12). To this purpose, it is preferred to laminate a thin cotton fabric or an otherwise skin-compatible fabric with a pre-fabricated adhesive layer such as, for example, the product Mefix of the firm Mölnlycke.

Preferred embodiments of the means according to the invention for the application of transdermally absorbable active substances are shown in the Figures of the attached drawing.

Figure 10A:
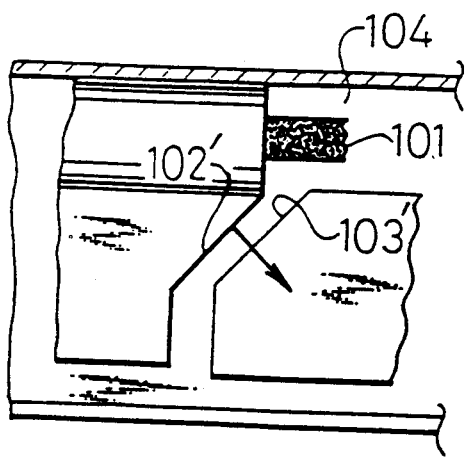
Figure 10B:
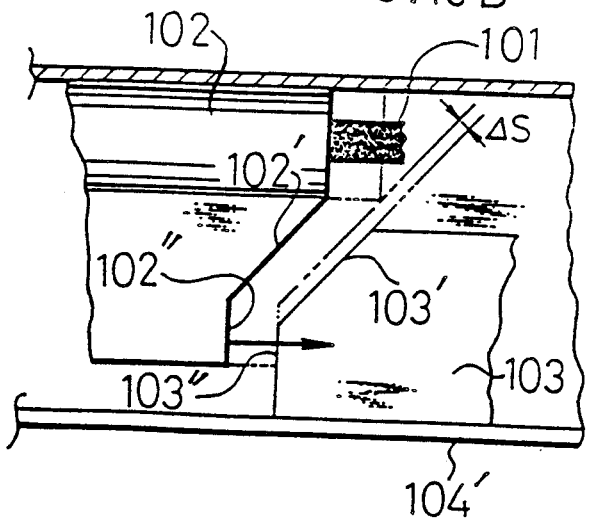

FIG. 10. shows the device of the present invention in the shape of a headband.

Figure 2:
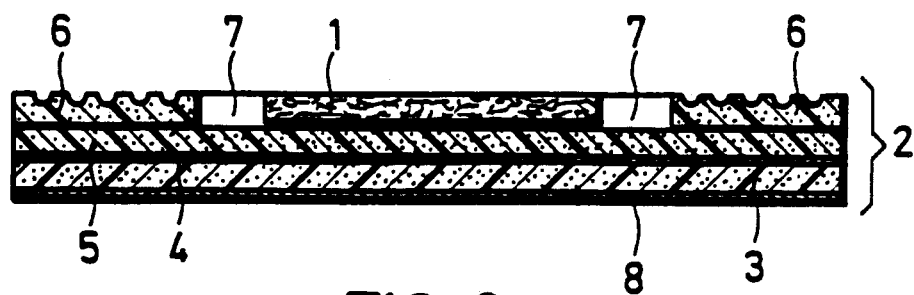
FIG. 2 shows a sectional view of these means.
Figure 3:
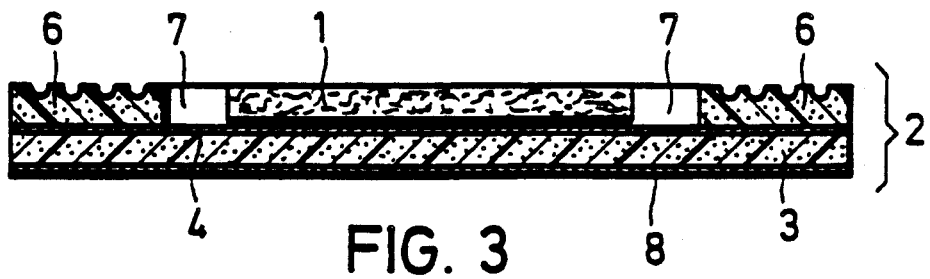
FIG. 3 and FIG. 4 show sectional views of simplified embodiments.
Figure 4:
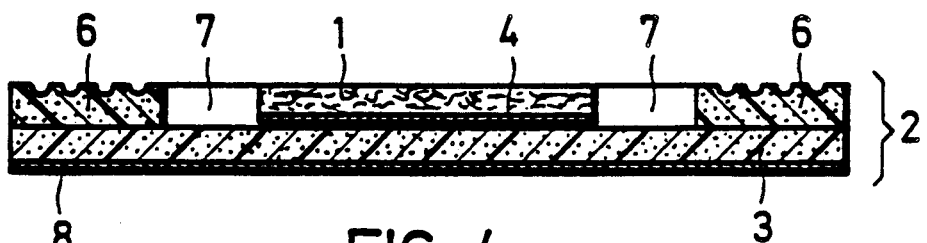
Figure 5:
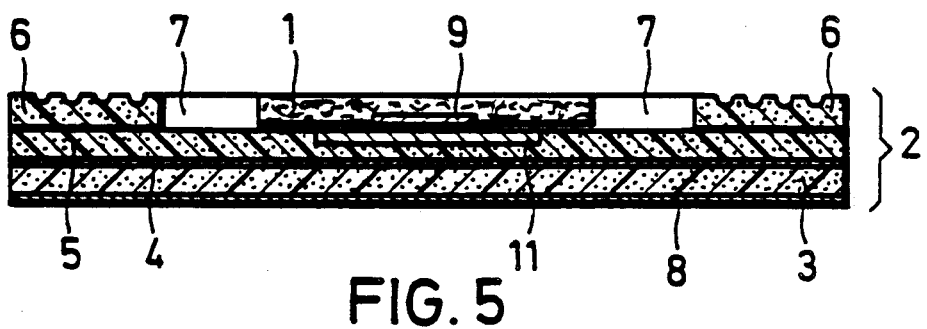
FIG. 5, FIG. 6 and FIG. 7 show embodiments derived from those according to the FIGS. 2, 3 and 4, wherein additional metal plates and magnetic foils have been incorporated for attaching the carrier to the support.
Figure 6:
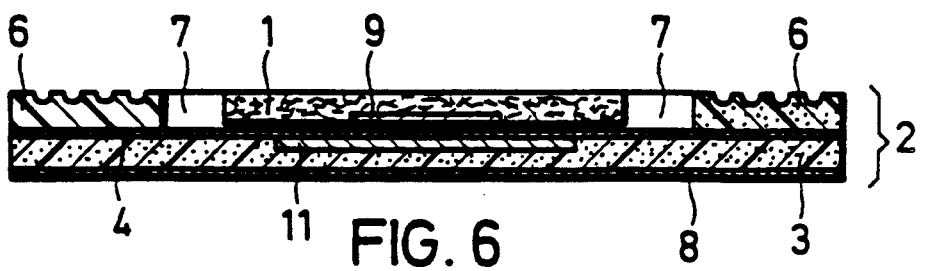
Figure 7:
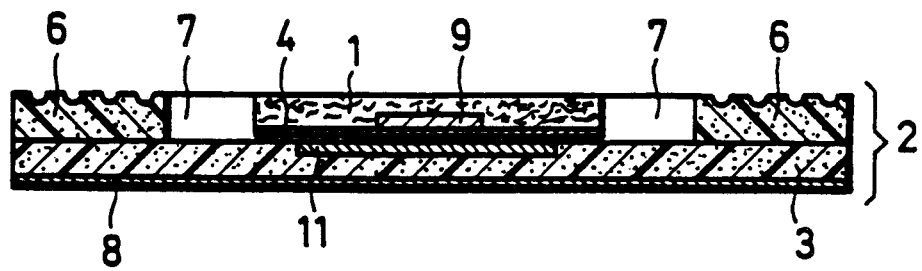
Figure 8:
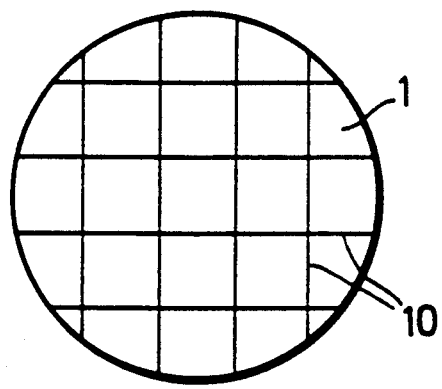
FIG. 8 shows a top plan view of a carrier (1) comprising a magnetically adhesive metal wire net.
Figure 9:
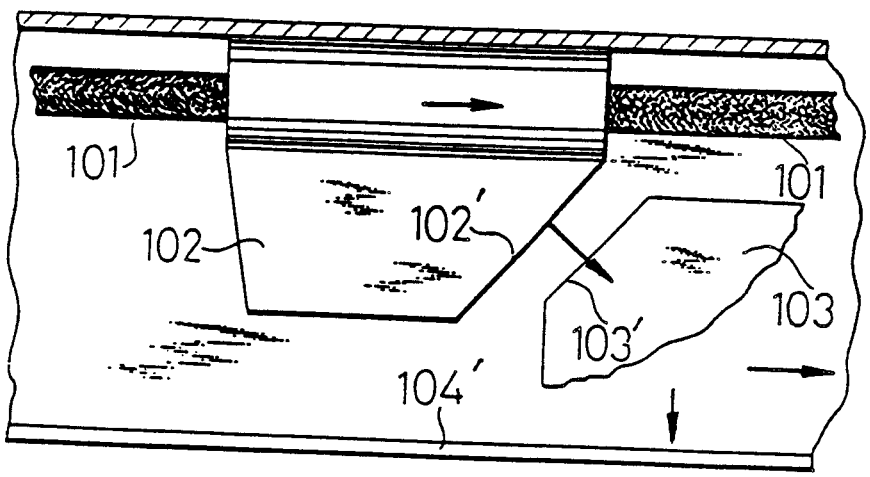
FIG. 9 shows an embodiment similar to FIG. 2, including an additional skin-compatible layer and Velcro hook-and-loop fasteners.

In the Figures, like parts have been designated by like reference numerals which have the following meanings:
(1) a carrier impregnated with a transdermally absorbable active substance;
(2) the entire support;
(3) a closed-cell polyethylene foam layer;
(4) a flexible heat-conductive metal foil;
(5) a closed-cell polyethylene foam layer which may optionally be colored;
(6) a closed-cell polyethylene foam layer which may optionally be surface-texturized or laminated with a fabric;
(7) a portion punched in pinked shape;
(8) a fabric layer made of Borsched nylon;
(9) a magnetically adhesive metal plate;
(10) a magnetically adhesive metal wire;
(11) a magnetic foil which, in stripe form, has been alternatingly positively and negatively permanently magnetized, the distance of the magnetized stripes from one another being between 3 and 10 mm;

In this preferred embodiment according to FIG. 2 the thickness of the polyethylene foam layer (3) is about 2 mm, the thickness of the polyethylene foam layer (5) is about 3 mm, and the thickness of the polyethylene foam layer (6) in original state is also 2 mm, and 1 to 1.8 mm in the surface-texturized state. Hence, the depth of the punched portion (7) is also about 1.8 mm. In the embodiments according to the FIGS. 3 and 4 the foam layers usually are somewhat thicker.

The removable and replaceable, skin-compatible plaster or the elastic bandage having a Velcro strip fastener for attaching the device of the invention to the skin have not been shown. Due to the fabric layer (8) which preferably consists of Borsched nylon, the self-adhesive plasters as well as the Velcro strip fasteners will adhere sufficiently firmly, while they may be removed again without any damage to the support (2), so that this support (2) may be frequently re-used.

Figure 1:
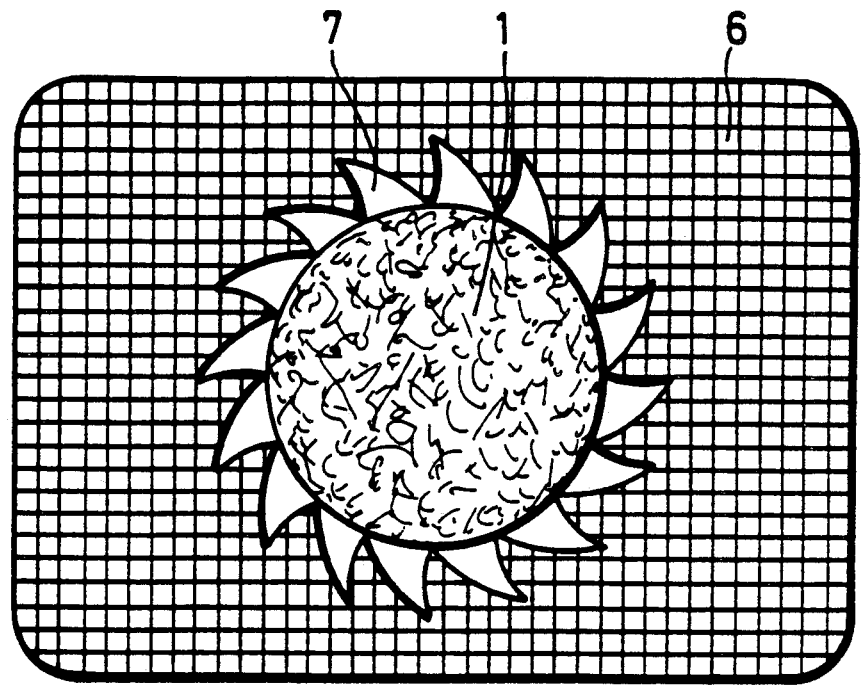
FIG. 1 shows a top plan view of the means in the shape of a plaster.

The punched portion (7) according to FIG. 1 is pinked in such a manner that saw-tooth-shaped aeration chambers are formed. Together with the inlaid carrier there is formed the image of flower leaves or of the aureole of a sun. However, basically there may be used linear or even wavily curved dents and, thus, rounded dents may be employed, if they are capable of sufficiently supporting the carrier (1) impregnated with the transdermally absorbable active substances.

For the manufacture of an appropriate head band a longitudinally extended support 5 to 30 cm in length and 2 to 4 cm in width is prepared wherein one or more portions (7) have been punched and into which appropriate smaller carriers (1) may be inserted. For the manufacture of pads, on the other hand, larger dimensions are chosen and also several portions (7) are punched into which appropriately larger carriers (1) may be inserted.

What is claimed is:

1. A device for application of a substrate to skin, comprising at least one absorptive carrier for applying a substrate to skin, and a laminate support housing the carrier comprising:
a first closed-cell polyethylene foam layer having a thickness of about 1 to 6 mm, said first foam layer including a foil-facing area and a laminate-contacting area defined on a first surface, and an opposite surface;

a second closed-cell polyethylene foam layer having a thickness of about 1 to 6 mm, said second foam layer including a laminate-contacting surface bonded to said laminate-contacting area of the first foam layer and an opposite, skin-contacting surface, wherein at least one portion of said second foam layer has been removed to define side walls surrounding an area housing the carrier, the housing area being at least as large as the surface area of the carrier; and a flexible heat-conductive metal foil, said metal foil including a first surface facing said foil-contacting surface of the first foam layer and an opposite surface facing said carrier.

2. A device as recited in claim 1, further comprising a transdermally absorbable active substance applied to said carrier.

3. A device as recited in claim 1, further comprising a fabric layer laminated onto the opposite surface of the first foam layer.

4. A device as recited in claim 1, further comprising a skin-compatible fabric covering the skin-contacting surface of the second foam layer.

5. A device as recited in claim 1, wherein said skin-contacting surface of the second foam layer has surface texturizations.

6. A device as recited in claim 1, wherein said carrier is a skin-compatible nonwoven fabric.

7. A device as recited in claim 1, wherein the total thickness of the laminate support is between 5 and 12 mm.

8. A device as recited in claim 1, wherein said metal foil is an aluminum foil having a thickness from 20 to 50 micrometers.

9. A method of applying a substance to skin, comprising:

placing the carrier in a laminate support comprising (i) a first closed-cell polyethylene foam layer having a thickness of about 1 to 6 mm, said first foam layer including a foil-facing area and a laminate-contacting area defined on a first surface, and an opposite surface, (ii) a second closed-cell polyethylene foam layer having a thickness of about 1 to 6 mm, said second foam layer including a laminate-contacting surface bonded to said laminate-contacting area of the first foam layer and an opposite, skin-contacting surface, wherein at least one portion of said second foam layer has been removed to define side walls surrounding an area housing the carrier, the housing area being at least as large as the surface area of the carrier, and (iii) a flexible heat-conductive metal foil, said metal foil including a first surface facing said foil-contacting surface of the first foam layer and an opposite surface facing said carrier; and applying the laminate support housing the carrier to the skin with the skin-contacting surface of the second foam layer facing the skin.

10. A method according to claim 9, wherein said substance is a transdermally absorbable active substance.

11. A method according to claim 10, wherein said transdermally absorbable active substance is an oil of a medicinal herb.

12. A method according to claim 9, wherein the laminate support further comprises a skin-compatible fabric covering the skin-contacting surface of the second foam layer.

13. A method according to claim 9, further comprising replacing the carrier with a fresh absorptive carrier by:

removing the laminate support housing the carrier from the skin;

removing the carrier from the laminate support;

applying a substance to a fresh carrier;

placing the fresh carrier in the laminate support; and applying the laminate support housing the fresh carrier to the skin with the skin-contacting surface of the second foam layer facing the skin.

14. A method according to claim 13, further comprising washing the laminate support after the step of removing the carrier from the laminate support.

* * * * *